United States Patent
Mequanint et al.

(10) Patent No.: US 11,227,156 B2
(45) Date of Patent: Jan. 18, 2022

(54) PERSONALIZED EYE OPENNESS ESTIMATION

(71) Applicant: QUALCOMM Incorporated, San Diego, CA (US)

(72) Inventors: Eyasu Zemene Mequanint, San Diego, CA (US); Shuai Zhang, San Diego, CA (US); Yingyong Qi, San Diego, CA (US); Ning Bi, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 605 days.

(21) Appl. No.: 16/239,352

(22) Filed: Jan. 3, 2019

(65) Prior Publication Data
US 2020/0218878 A1    Jul. 9, 2020

(51) Int. Cl.
| | | |
|---|---|---|
| *G06K 9/00* | (2006.01) | |
| *G06T 7/00* | (2017.01) | |
| *A61B 5/11* | (2006.01) | |
| *G06F 21/32* | (2013.01) | |
| *G08B 21/18* | (2006.01) | |
| *A61B 5/1171* | (2016.01) | |

(52) U.S. Cl.
CPC .......... *G06K 9/0061* (2013.01); *A61B 5/1103* (2013.01); *A61B 5/1128* (2013.01); *A61B 5/1176* (2013.01); *G06F 21/32* (2013.01); *G06K 9/00604* (2013.01); *G06K 9/00845* (2013.01); *G06T 7/00* (2013.01); *G08B 21/182* (2013.01)

(58) Field of Classification Search
CPC ............. G06K 9/0061; G06K 9/00604; G06K 9/00845; G06K 9/00; G06T 7/00
See application file for complete search history.

(56) References Cited

U.S. PATENT DOCUMENTS

2018/0240319 A1*   8/2018   Wulf .................. B60Q 9/00

OTHER PUBLICATIONS

Gou, Chao, et al. "A joint cascaded framework for simultaneous eye detection and eye state estimation." Pattern Recognition 67 (2017): 23-31. (Year: 2017).*

* cited by examiner

*Primary Examiner* — Menatoallah Youssef
(74) *Attorney, Agent, or Firm* — Holland & Hart LLP

(57) ABSTRACT

Methods, systems, and devices for personalized (e.g., user specific) eye openness estimation are described. A network model (e.g., a convolutional neural network) may be trained using a set of synthetic eye openness image data (e.g., synthetic face images with known degrees or percentages of eye openness) and a set of real eye openness image data (e.g., facial images of real persons that are annotated as either open eyed or closed eyed). A device may estimate, using the network model, a multi-stage eye openness level (e.g., a percentage or degree to which an eye is open) of a user based on captured real time eye openness image data. The degree of eye openness estimated by the network model may then be compared to an eye size of the user (e.g., a user specific maximum eye size), and a user specific eye openness level may be estimated based on the comparison.

20 Claims, 7 Drawing Sheets

PERSONALIZED EYE OPENNESS ESTIMATION

BACKGROUND

The following relates generally to object recognition (e.g., detecting a degree to which an eye is open), and more specifically to personalized (e.g., user specific) eye openness estimation.

Object recognition may refer to a field of computer vision for finding and identifying objects in an image or video sequence. As an example of object recognition, facial recognition may refer to a process used to identify or verify a person (e.g., from a digital image, a frame of a video clip, etc.) based on one or more facial features. Generally, facial features may be extracted from the image and compared with features stored in a database. Additionally or alternatively, the extracted facial features may be fed to a classifier, which may in turn generate an identity hypothesis based on the input features.

In some computer vision applications, techniques for eye openness detection may take a face image as input, extract features around an eye (e.g., or both eyes), and use an algorithm to determine if the eye is open or closed. Likewise, techniques for blink detection may take a set of video frames as input, and may extract features around an eye (e.g., or eyes) to estimate variations in the degree of eye openness (e.g., to determine if the eyes have blinked). Such techniques for eye openness detection may be implemented in mobile devices (e.g., for intelligent picture taking, face recognition, user liveness detection), vehicles (e.g., for driver drowsiness detection, advanced driving assistance systems (ADAS)), etc.

In some cases, conventional approaches for detection of open, closed, or blinking eyes may only detect two states of the eyes (e.g., either an open state, or a closed state), which may be insufficient for some applications. Further, some eye openness detection techniques may use video or a sequence of frames for decision making, which may result in significant system delays (e.g., as the system may need to process or consider the duration of a video clip or several images in the sequence of frames for any decision making). As existing techniques for eye openness detection may, in some cases, be deficient, improved techniques for eye openness estimation may be desired.

SUMMARY

The described techniques relate to improved methods, systems, devices, or apparatuses that support personalized (e.g., user specific) eye openness estimation. Generally, aspects of the described techniques provide for a network model (e.g., a trained convolutional neural network) for multi-stage eye openness detection, which may be implemented on an embedded device (e.g., a wireless device, a driver monitoring system, etc.). The described techniques may further provide for identification (e.g., estimation) of the user's eye size (e.g., a maximum eye openness level of a user), such that the degree of eye openness estimated by the trained network may be adapted to estimate a personalized or user specific eye openness level.

A network, such as a convolutional neural network, may be trained using a set of synthetic eye openness image data (e.g., synthetic face images with known degrees or percentages of eye openness) and a set of real eye openness image data (e.g., facial images of real persons that are annotated as either open eyed or closed eyed). In some cases, the network may include a shared convolution block and two fully connected blocks. A loss function for cross domain adaptation (e.g., between the synthetic data and real data) for effective network training is also described. The network model may then be implemented on a device for efficient and effective eye openness estimation. For example, the device may estimate, using the network model, a multi-stage eye openness level (e.g., a percentage or degree to which an eye is open) of a user based on captured real time eye openness image data, such as a single image, a video clip, a sequence of images, etc.

According to additional aspects of the described techniques, the degree of eye openness estimated by the network model may then be compared to an eye size of the user, and a user specific eye openness level may be estimated based on the comparison. For example, a device may identify a maximum eye openness level of a user during enrollment (e.g., during an enrollment procedure). The enrollment procedure may include a user maximum eye size input procedure, a user maximum approximate eye size selection procedure, a device maximum eye size estimation from enrolled faces, an initial image capture that is used for device maximum user eye size estimation, etc. In some cases, a maximum eye size or maximum eye openness level of a user may be referred to as a user specific eye size, a user specific baseline eye size, etc. In some cases (e.g., when the degree of eye openness estimated by the network model exceeds the maximum eye openness level), the maximum eye openness level may be updated (e.g., set to equal the degree of eye openness estimated by the network model).

A method of detecting a degree to which an eye is open is described. The method may include capturing real time eye openness image data using a sensor, and estimating a degree of eye openness based on the real time eye openness image data and a set of synthetic eye openness image data including known levels of eye openness. The method may further include identifying a maximum eye openness level of a user during an enrollment procedure (e.g., where the maximum eye openness level is based on a personalized eye size of the user) and estimating a user specific eye openness level based on the estimated degree of eye openness and the maximum eye openness level of the user. The method may then include triggering an action (e.g., an authentication action, an unlocking action, an alarm sounding action, etc.) based on the estimated user specific eye openness level.

An apparatus for detecting a degree to which an eye is open is described. The apparatus may include a processor, memory in electronic communication with the processor, and instructions stored in the memory. The instructions may be executable by the processor to cause the apparatus to capture real time eye openness image data using a sensor, estimate a degree of eye openness based on the real time eye openness image data and a set of synthetic eye openness image data including known levels of eye openness, identify a maximum eye openness level of a user during an enrollment procedure, where the maximum eye openness level is based on a personalized eye size of the user, estimate a user specific eye openness level based on the estimated degree of eye openness and the maximum eye openness level of the user, and trigger an action based on the estimated user specific eye openness level.

Another apparatus for detecting a degree to which an eye is open is described. The apparatus may include means for capturing real time eye openness image data using a sensor, estimating a degree of eye openness based on the real time eye openness image data and a set of synthetic eye openness image data including known levels of eye openness, identifying a maximum eye openness level of a user during an enrollment procedure, where the maximum eye openness level is based on a personalized eye size of the user, estimating a user specific eye openness level based on the estimated degree of eye openness and the maximum eye openness level of the user, and triggering an action based on the estimated user specific eye openness level.

A non-transitory computer-readable medium storing code for detecting a degree to which an eye is open is described. The code may include instructions executable by a processor to capture real time eye openness image data using a sensor, estimate a degree of eye openness based on the real time eye openness image data and a set of synthetic eye openness image data including known levels of eye openness, identify a maximum eye openness level of a user during an enrollment procedure, where the maximum eye openness level is based on a personalized eye size of the user, estimate a user specific eye openness level based on the estimated degree of eye openness and the maximum eye openness level of the user, and trigger an action based on the estimated user specific eye openness level.

Some examples of the method, apparatuses, and non-transitory computer-readable medium described herein may further include operations, features, means, or instructions for determining that the user specific eye openness level may be greater than the maximum eye openness level, and updating the maximum eye openness level based on the determination. Some examples of the method, apparatuses, and non-transitory computer-readable medium described herein may further include operations, features, means, or instructions for determining the user may have satisfied a facial recognition condition, where the maximum eye openness level may be updated based on the determination.

In some examples of the method, apparatuses, and non-transitory computer-readable medium described herein, the degree of eye openness may be estimated based on convolution of the real time eye openness image data and the set of synthetic eye openness image data. Some examples of the method, apparatuses, and non-transitory computer-readable medium described herein may further include operations, features, means, or instructions for receiving a maximum eye openness level input from the user, where the maximum eye openness level may be identified based on the maximum eye openness level input. In some examples of the method, apparatuses, and non-transitory computer-readable medium described herein, the maximum eye openness level may be identified based on the real time eye openness image data.

Some examples of the method, apparatuses, and non-transitory computer-readable medium described herein may further include operations, features, means, or instructions for performing an authentication procedure based on the triggering, where the estimated user specific eye openness level exceeds a threshold. In some examples of the method, apparatuses, and non-transitory computer-readable medium described herein, triggering the action may include operations, features, means, or instructions for triggering an alarm based on the estimated user specific eye openness level, where the estimated user specific eye openness level may be below a threshold.

In some examples of the method, apparatuses, and non-transitory computer-readable medium described herein, the user specific eye openness level includes a percentage of eye openness. In some examples of the method, apparatuses, and non-transitory computer-readable medium described herein, the real time eye openness image data includes a single image. Some examples of the method, apparatuses, and non-transitory computer-readable medium described herein may further include operations, features, means, or instructions for estimating the degree of eye openness based on a mean squared error (MSE) function, a binary loss function, and a distribution loss function.

DETAILED DESCRIPTION

Figure 1:
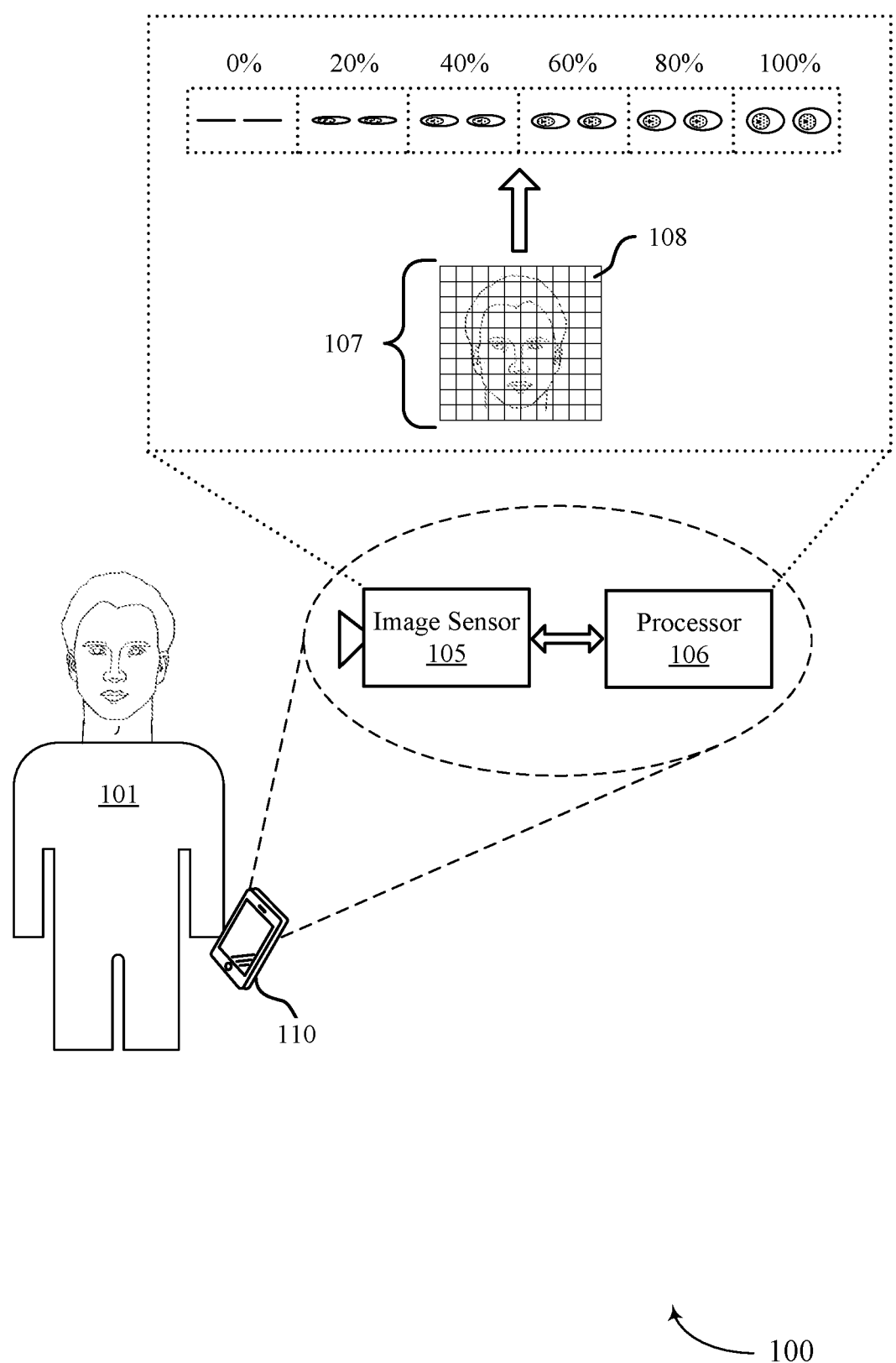
FIG. 1 illustrates an example of a system for detecting a degree to which an eye is open that supports personalized eye openness estimation in accordance with aspects of the present disclosure.

Object recognition refers to a field of computer vision for finding and identifying objects in an image or video sequence. Though aspects of the following are described in the context of eye openness detection, it is to be understood that the described techniques may be extended to recognition of other objects in an image (e.g., animals, inanimate objects, other facial features, etc.) without deviating from the scope of the present disclosure. Eye openness detection (e.g., ocular detection, user awareness detection, etc.) may refer to the process of identifying or verifying an eye openness stage (e.g., as open or closed) from a digital image or video frame. For example, in some computer vision applications, techniques for eye openness detection may take a face image as input, extract features around an eye (e.g., or both eyes), and use an algorithm to determine if the eye is open or closed. Likewise, techniques for blink detection may take a set of video frames as input, and may extract features around an eye (e.g., or eyes) to estimate variations in the degree of eye openness (e.g., to determine if the eyes have blinked). Such techniques for eye openness detection may be implemented in mobile devices (e.g., for intelligent picture taking, face recognition, user liveness detection), vehicles (e.g., driver drowsiness detection, advanced driving assistance system (ADAS)), etc.

Existing approaches for eye openness detection that only detect and consider two states of the eyes (e.g., either an open state, or a closed state) may be insufficient for some applications. For example, some driver monitoring systems (e.g., employing mere open, closed, or blinking eye detection) may be inadequate in detection of drowsy drivers who may be in a fatigue induced state, semi-sleeping state, inebriated state, eyes half open state, etc. In cases where blink detection techniques are implemented, video or sequences of frames used for such decision making may introduce significant system delays (e.g., which may be intolerable in scenarios where a driver has fallen asleep).

Moreover, results of such control systems that rely on blink detection may be inconsistent, as it may be difficult to catch fast blink actions by a user.

The described techniques may provide for multi-stage eye openness detection (e.g., detection of eye openness at 0%, 25%, 50%, 75%, 100% levels). For example, real time eye openness image data (e.g., an image of a user's face or an image of a user's eyes) may be processed using a trained neural network to estimate a degree of eye openness. The network, such as a convolutional neural network, may be trained using a set of synthetic eye openness image data (e.g., synthetic face images with known degrees or percentages of eye openness) and a set of real eye openness image data (e.g., facial images of real persons that are annotated as either open eyed or closed eyed). An innovative loss function for cross domain adaptation between synthetic data and real (e.g., open/closed annotated) data may include a mean squared error (MSE) function, a binary loss function, and a distribution loss function. As such, a device may capture real time eye openness image data and may implement the network model to estimate a degree (e.g., level, percentage, etc.) of eye openness.

Such multi-stage eye openness detection techniques may provide for more granular eye openness estimations, which may provide for increased performance and flexibility of some eye openness detection applications. For example, the described techniques may be implemented in driver monitoring systems to detect drivers with decreased eye openness due to, for example, fatigue, inebriation, sleepiness, etc. (e.g., compared to the more limited scenario of detection of drivers with closed eyes). In general, increased granularity in eye openness detection outputs (e.g., realized using the multi-stage eye openness detection techniques described herein) may provide for improvements in existing eye openness applications (e.g., such as mobile phone and vehicle safety applications) as well as developments in new applications (e.g., which may utilize the more analog-link outputs of the detection techniques). For example, systems may be designed to trigger actions based on certain levels, other than open or closed, of eye openness (e.g., a pair of smart glasses may focus or a display may zoom or enlarge text based on a user squinting their eyes).

In some cases, the neural network may be trained off device (e.g., offline on some different server, on a local machine/computer, etc.), and a trained processor or trained chipset may be implemented in a sensor system of some device. A sensor may collect real time eye openness image data (e.g., a single image, a video clip, a sequence of images, etc.) that may be processed or analyzed by the trained neural network. Systems utilizing such sensors and trained neural networks may not be limited to a single input type (e.g., the described techniques may process a single image, a video clip, a sequence of images, etc.). Therefore, control system delay may be more readily controllable as user eye openness image data input types for such eye openness detection systems may be more flexible. For example, in implementations where a single image is used for multi-stage eye openness detection, real-time training delays may be saved (e.g., compared to real-time delays realized in other eye openness detection systems from processing and comparing several images or frames).

Further, the described techniques may provide for user specific (e.g., personalized) multi-stage eye openness detection. For example, multi-stage eye openness detection may be personalized based on the individual's eye size (e.g., the degree of eye openness may be estimated relative to a user's specific eye size). For example, a single image (e.g., or in some cases a video clip or a sequence of images) may be processed by the trained network to estimate a degree of eye openness. The degree of eye openness estimation may then be compared to a personalized maximum eye openness level (e.g., a user specific eye size identified during an enrollment procedure). In some cases (e.g., when the degree of eye openness estimated by the network model exceeds the user's maximum eye openness level), the maximum eye openness level may be updated (e.g., set to equal the degree of eye openness estimated by the network model). Such may result in improved eye openness detection reliability and improved eye openness estimation accuracy. For example, false eye openness determinations by conventional eye openness detection systems may be reduced (e.g., as in some cases a user with small eyes may be falsely detected as having closed eyes in systems that do not account for the user').

Aspects of the disclosure are initially described in the context of a system for personalized (e.g., user specific) multi-stage eye openness estimation. An example network architecture and an example flowchart each supporting personalized eye openness estimation in accordance with aspects of the present disclosure are then described. Aspects of the disclosure are further illustrated by and described with reference to apparatus diagrams, system diagrams, and flowcharts that relate to personalized eye openness estimation FIG. 1 illustrates an example of a system 100 (e.g., a driver monitoring system, a mobile device authentication system, etc.) that supports personalized eye openness estimation in accordance with aspects of the present disclosure. System 100 may include at least an image sensor 105 and a user 101. The image sensor 105 (e.g., in communication with a processor 106) may capture an image 107 comprising a plurality of pixels 108. In some cases, the image sensor may capture an image 107 of a face of user 101, and may perform eye openness detection techniques described herein in coordination with a processor 106. In some examples, the image sensor 105 and processor 106 may be implemented in a device 110 (e.g., a mobile device, some other user authentication device, a vehicle, a driver monitoring system, etc.). Such examples are given for illustrative purposes only. As discussed herein, the described techniques may be implemented in various applications.

Techniques described with reference to aspects of system 100 are done so for exemplary purposes only, and are not intended to be limiting in terms of the applicability of the described techniques. That is, the techniques described may be implemented in, or applicable to, other imaging examples (e.g., other examples of image processing or camera based applications), without departing from the scope of the present disclosure. For example, the techniques described may generally be applied to images of other features or objects, other types of image data (e.g., a single image as shown, a video clip, a sequence of images, etc.), other applications or scenarios, etc.

As used herein, a device 110 may generally refer to any device with suitable hardware (e.g., a camera or image sensor 105, a chip or processor 106, etc.) for performing the described techniques. In some cases, device 110 may refer to a camera, a mobile device, a wireless device, a remote device, a handheld device, a subscriber device, a personal electronic device such as a cellular phone, a personal digital assistant (PDA), a tablet computer, a laptop computer, a personal computer, or some other suitable terminology. Further examples of devices 110 that may implement one or more aspects of personalized eye openness detection techniques may include camcorders, webcams, driver monitoring systems (e.g., a vehicle), computer monitors, cockpit controls and/or displays, camera view displays (such as the display of a rear-view camera in a vehicle), etc.

In some cases, image sensor 105 may refer to a complementary metal oxide semiconductor (CMOS) image sensor, a charge-coupled device (CCDs), etc. used in digital imaging applications to capture an image, a video clip, a sequence of images, etc. An image sensor 105 may include an array of sensors. Each sensor in the pixel sensor array may include at least one photosensitive element for outputting a signal having a magnitude proportional to the intensity of incident light or radiation contacting the photosensitive element. When exposed to incident light reflected or emitted from an object or scene, each sensor in the pixel sensor array may output a signal having a magnitude corresponding to an intensity of light at one point in the object (e.g., at an image capture time). The signals output from each photosensitive element may be processed (e.g., by the image sensor 105 and/or processor 106) to form an image 107 representing the captured object. In general, a pixel brightness measurement or a pixel value from an image sensor 105 (e.g., from pixel sensor array) may correspond to a pixel intensity value, RGB values of a pixel, infrared values of a pixel, or any other parameter associated with light (e.g., or the image being captured, the picture being taken, etc.). A pixel sensor array may include one or more photosensitive elements for measuring such information. In some examples, the photosensitive elements may have a sensitivity to a spectrum of electromagnetic radiation (e.g., including the visible spectrum of electromagnetic radiation, infrared spectrum of electromagnetic radiation, etc.). For example, the at least one photosensitive element may be tuned for sensitivity to a visible spectrum of electromagnetic radiation (e.g., by way of depth of a photodiode depletion region associated with the photosensitive element).

An image 107 (e.g., a digital image captured by the image sensor 105) may comprise a plurality of pixels 108. Image 107 may be obtained in a variety of ways in accordance with the present disclosure. For example, image 107 may be obtained by image sensor 105, such as a camera, which is interoperable with a processor 106 capable of implementing aspects of the present disclosure. The device 110 may process digital image 107 by applying operations to pixels 108 (e.g., to extract facial features which may be used for eye openness detection or eye openness estimation). Examples of such processing may include face detection, face tracking, facial landmark detection (e.g., eye detection), face normalization, feature extraction, identification/verification, etc. For example, in some cases, the image sensor 105 may signal or pass image 107 information (e.g., pixel 108 information) to the processor 106. The processor 106 (e.g., one or more driver circuits for image processing) may then process the information collected by the image sensor 105 to estimate a user specific eye openness level from the image 107 information.

For example, the processor 106 may process pixels 108 to identify a region of the image 107 representing an eye of the user 101, compare the eye of the user 101 to a database, process the eye of the user 101 using a trained neural network, estimate a degree of eye openness, estimate a user specific (e.g., personalized) maximum eye openness, estimate a user specific degree of eye openness, etc., as described in more detail below. In some cases, the processor 106 may refer to a general central processing unit (CPU), a dedicated piece of hardware, a system on chip (SoC), an installed chipset, etc. Further, the device 110 may include electrical connections associated with the image sensor 105, the one or more drivers (e.g., the processor 106), etc., and may provide connections between the image sensor 105 and the processor 106. In some examples, a general processor of the device may perform aspects of the processor 106.

In some cases, a device 110 may include other components, such as a display (e.g., for displaying the image, the results of the eye openness estimation, etc.), an alarm (e.g., that may be triggered by the processor 106), a transceiver (e.g., for transmitting or receiving information), etc., depending on the application. For example, a device 110 when referring to a mobile device may include different components (e.g., in addition to the image sensor 105 and processor 106) compared to a device 110 when referring to a driver monitoring system. In general, a device 110 may include any number of various components depending on the application of the techniques described herein.

In some cases, conventional approaches for detection of open, closed, or blinking eyes may only detect two states of the eyes (e.g., either an open state, or a closed state), which may be insufficient for some applications. For example, some driver monitoring systems (e.g., employing open, closed, or blinking eye detection techniques) may be inadequate in detection of drowsy drivers who may be in a fatigue induced state, semi-sleeping state, inebriated state, eyes half open state, etc. In cases where blink detection techniques are implemented, video or sequences of frames used for such decision making may introduce significant system delays (e.g., which may be intolerable in scenarios where a driver has fallen asleep). Moreover, results of such control systems that rely on blink detection may be inconsistent, as it may be difficult to catch fast blink actions by a user.

As described herein, an image 107 may be processed for multi-stage eye openness estimation using a trained neural network (e.g., a convolutional neural network). Generally, a convolutional neural network may refer to a class of feedforward artificial neural networks in which the connectivity pattern between nodes of the neural network resembles that of neurons in various biological processes. For example, the convolutional neural network may process the image 107 using a number of layers to generate feature maps, which may be analyzed (e.g., and in some cases combined) to detect, classify, or estimate a degree of eye openness. In some cases, training of the neural network may be computationally intensive, utilizing large amounts of memory, processing, power, time, etc. As such, in some cases, the neural network may be trained off device (e.g., offline, on a different server, on a local machine or another computer, etc.). In such cases, the trained processor 106 (e.g., a trained modem or trained chipset in communication with processor 106) may be implemented in or loaded onto the device 110 (e.g., on to a sensor driver of the device 110). Therefore, devices 110 may benefit from using an image sensor 105 and the trained neural network for faster, more input flexible, and more granular output eye openness detection techniques. Though described in the context of ocular detection, the framework described below may additionally or alternatively be extended to recognize other facial attributes, or manipulations of other facial attributes (e.g., mouth openness, etc.).

In some examples, eye openness techniques described herein may be implemented in facial authentication systems. For example, such systems may be operable to reject (i.e., not recognize) faces with closed eyes, which may provide additional security (e.g., by preventing unauthorized access to a device while a registered user is sleeping). For face verification, the provided face image (e.g., digital image 107) may be compared with one or more registered faces.

This comparison may be done via metric distance (e.g., Euclidean distance) comparison or using a classifier trained with one or more registered faces of a given person. Face verification may be related to access control for a device and may therefore be associated with higher accuracy than face identification in some examples. In some cases, for multi-stage eye openness estimation, an eye region of image 107 may be compared with the synthetic data and real data (e.g., processed by the trained neural network).

The techniques described herein may implement deep learning to estimate degrees of eye openness (e.g., of a user 101). A network (e.g., a neural network, a convolutional neural network, etc.) may be trained using synthetic data with known levels of eye openness and real data having either open eye or closed eye annotation. For example, synthetic data may include sequences of data with known levels of eye openness (e.g., images of eye portions of synthetic faces with labeled degrees of eye openness, such as 0%, 10%, 20%, 30%, etc.). Real data may include sequences of real data of different persons with either open eyes or closed eyes (e.g., images of eye portions of real faces with open eye or closed eye annotation). Cross domain adaptation between the synthetic data and the real data for effective network training may utilize an innovative loss function (e.g., including a MSE loss term for accurately predicting level of openness on synthetic data, a binary loss term for accurately predicting binary labeled real data, and a distribution loss term for controlling domain mismatch between synthetic data and real data). Such a network for estimation of multi-stage eye openness is further described below, with reference to FIG. 2.

Further, the techniques described herein may provide a framework for multi-stage eye openness estimation based on the personalized eye size of the user (e.g., based on a user specific eye size). Considering user specific eye size when estimating degree of eye openness (e.g., estimating user specific eye openness) may reduce false or inaccurate eye openness estimations otherwise resulting from the variance in the physical size of an eye from person to person. For example, a person with small eyes may be wide awake with an eye openness similar to a person with large eyes that is drowsy eyed (e.g., or relatively close-eyed). A device 110 may thus use a maximum personalized eye size estimation of a user 101 as a reference, and may adaptively update (e.g., scale) estimated eye openness estimation results from the network to estimate a user specific eye openness more accurately.

For example, a device 110 may identify a maximum eye openness of a user 101 during an enrollment procedure (e.g., maximum eye openness or a baseline user specific eye size may be estimated from enrolled faces, for each enrolled user, etc.). In other examples, a baseline user specific eye size (e.g., a maximum eye openness level of a user 101) may be estimated from a first capture set of images or video frames. Additionally or alternatively, the baseline user specific eye size may be estimated from an interactive enrollment procedure where the user 101 is asked to provide some thresholds on an eye openness level curve generated from the user (e.g., or the user may indicate a small, medium, or large eye size, may select from a sequence of images illustrating different eye sizes, etc.). In some examples, the system may revise the thresholds if the amount of eye size/degree of openness is raised to a different level. Such a framework for multi-stage eye openness estimation based on the personalized eye size of the user is further described below, with reference to FIG. 3.

Figure 2:
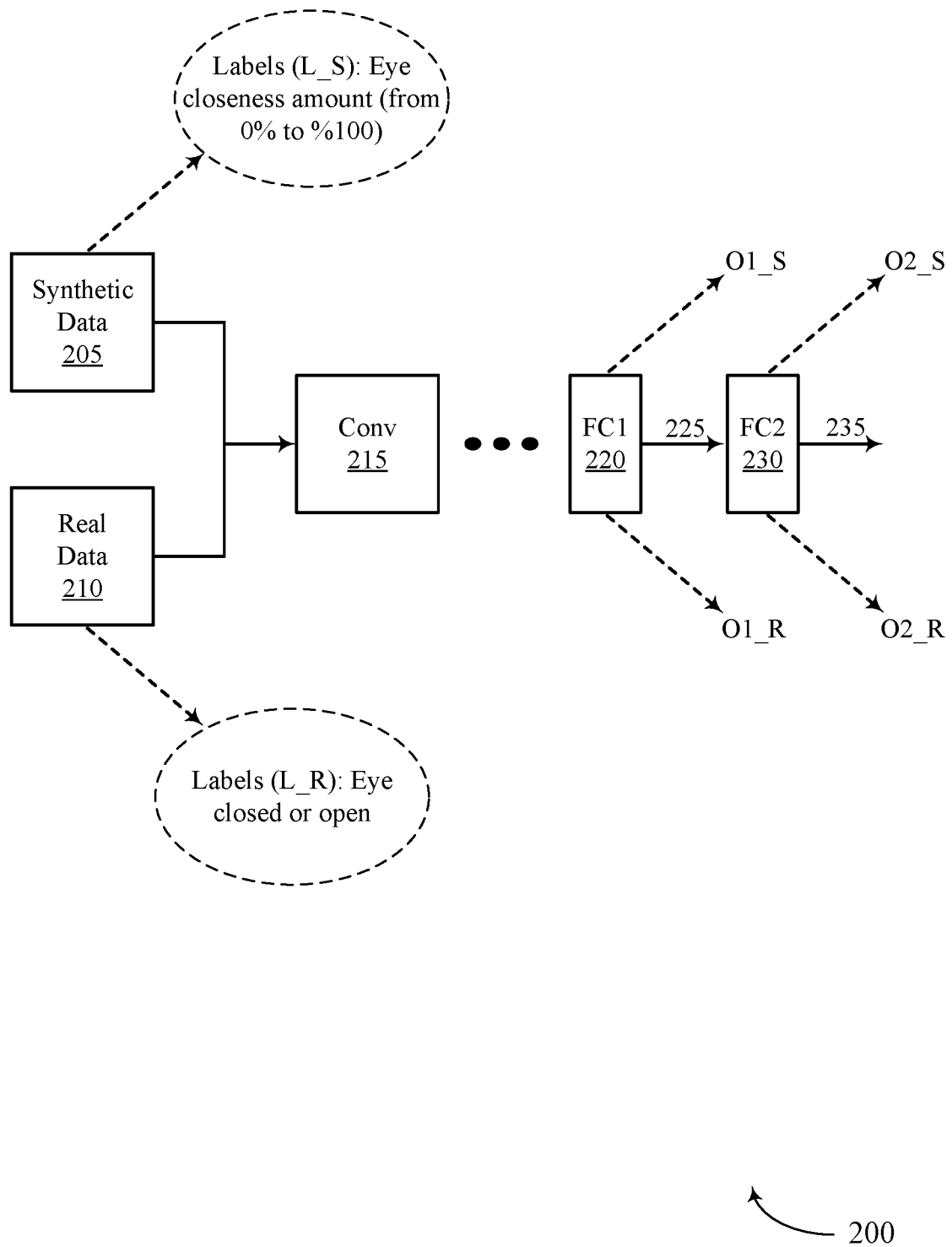
FIG. 2 illustrates an example of a network architecture that supports personalized eye openness estimation in accordance with aspects of the present disclosure.

FIG. 2 illustrates an example of a network architecture 200 (e.g., a network model) that supports personalized eye openness estimation in accordance with various aspects of the present disclosure. For example, the network architecture may illustrate a process flow that may be implemented (e.g., by a processor of a device 110) as part of a neural network for eye openness estimation. In some cases, network architecture 200 may include an input block (e.g., that takes in both synthetic data 205 and real data 210), a shared convolution block (CONV) 215, and two fully connected blocks (e.g., FC1 220 and FC2 230). As described in more detail below, the network may be trained using synthetic data 205 and real data 210, and cross domain adaptation between the synthetic data 205 and real data 210 for effective network training may use an innovative loss function.

In general, the convolution block 215 may perform a series of convolutions, pooling operations, etc. during which features may be detected (e.g., eye openness features). For example, convolution may be performed on the input data with the use of a filter (e.g., which may be referred to as a kernel) to then produce a feature map. In generally, any number of convolutions may be performed on the input, where each operation may use a different filter (e.g., resulting in different feature maps). Ultimately, such feature maps may be combined as the final output of the convolution layer. The fully connected layers (e.g., FC1 220 and FC2 230) may serve as a classifier on top of these extracted features. The network architecture 200 is shown with a shared convolution block 215, and two fully connected blocks (e.g., FC1 220 and FC2 230). Such an illustration is not intended to limit the scope of the present disclosure. The network training techniques described herein may be applied to other convolutional neural network configurations or other network architectures by analogy, without departing from the scope of the present disclosure.

A mixed batch of synthetic data 205 and real data 210 (e.g., real face images with open eye or closed eye annotation) may be fed into the convolutional neural network (e.g., into the convolution block 215). For example, a series of mixed synthetic images and real images may be fed into the convolution block 215. As mentioned above, synthetic face images may be associated with known degrees of eye openness. For example, each synthetic data 205 (e.g., each synthetic face image) may be labeled with the data's known eye closeness amount (L_S). The label L_S may range from 0% (e.g., a closed eye) to 100% (e.g., a synthetic maximum eye openness). That is, a synthetic face image generated with half open eyes may be labeled with L_S=50%. Further, real face images used to train the system (e.g., a collection of images of random faces of real persons, or selected faces of real persons, etc.) may be annotated as either open eye or closed eye. For example, each real data 210 (e.g., each real face image) may be annotated with an eye open or eye closed annotation (L_R).

The convolution block 215 may combine any number of different convolution layers. The same set of filters may be applied regardless of the input (e.g., the same filters may be applied regardless of whether synthetic data 205 or real data 210 is input to the convolution block 215).

The first fully connected block, FC1 220, may output a feature vector 225. For example, for a synthetic data 205 input, FC1 220 may output a synthetic image feature vector (O1_S). For a real data 210 input, FC1 220 may output a real image feature vector (O1_R). For example, in some cases, a feature vector (e.g., O1_S or O1_R) may be a vector of size 256. In general, FC1 220 may refer to a first fully connected layer that may be used to generate a feature vector (e.g., a candidate feature vector in the case of training or a probe feature vector in the case of object recognition).

The second fully connected block, FC2 230, may transform the feature vector 225 into a scalar indicative of a degree of eye openness. That is, the feature vector 225 output from FC1 220 may be input into FC2 230, and FC2 230 may transform the feature vector 225 (e.g., a large vector indicative of eye feature(s)) into a scalar indicative of eye openness. The output of FC2 230 may thus estimate the degree of eye openness for a given input (e.g., for an input processed by the network architecture 200). For example, for a synthetic data 205, FC2 230 may transform O1_S into a scalar output (O2_S) indicating a degree of eye openness of the synthetic image. For a real data 210, FC2 230 may transform O1_R into a scalar output (O2_R) indicating a degree of eye openness of the real image.

The loss function for cross-domain network training may include an MSE loss term, a binary loss term, and a distribution loss term. The MSE, loss for accurately predicting level of eye openness on synthetic data, may be represented as $$\text{Loss1} = \text{MSE}(O2\_S, L\_S)$$

The binary loss, for accurately predicting binary labeled (e.g., open eye or closed eye labeled) real data with a closed threshold (CT), may be represented as $$\text{Loss2} = \frac{1}{N} \sum_i (\|O2\_R_i\|^2 * (1 - L\_R_i) + \max((CT - O2\_R_i), 0) * L\_R_i)$$

The distribution loss, for controlling domain mismatch between synthetic and real data, may be represented as $$\text{Loss3} = \text{abs}([\text{mean}(O1\_S) - \text{mean}(O1\_R)]) + \text{abs}([\text{Var}(O1\_S) - \text{Var}(O1\_R)])$$

As previously discussed, in the above three equations:
O1_S=FC1 220 vector output of the synthetic data
O1_R=FC1 220 vector output of the real data
O2_S=FC2 230 scalar output of the synthetic data
O2_R=FC2 230 scalar output of the real data
CT=Closeness threshold (e.g., a hyper parameter)
(e.g., where O2 is a scalar which may represent the closeness amount, and O1 is a feature vector of size 256).

Training the network (e.g., network architecture 200) using a loss function (e.g., an aspect of convolutional neural network backpropagation, which in some cases may be referred to as a cost function) including the three terms above may result in more accurate eye openness estimation by a device (e.g., by a device processing real time eye openness image data with such a trained modem or chipset). For example, capturing of real time eye openness image data, estimation of a degree of eye openness, identification of a maximum eye openness level of a user, estimation of a user specific eye openness level, etc., may be performed by communicatively coupled hardware within a device based at least in part on the network architecture 200. As discussed, in some examples, the network training may be performed off device, and a trained modem (e.g., in a chipset), driver, or other device hardware may be included in a device. In some cases, illustrated arrows may represent signals or information that may be communicated via electrical connections between device hardware.

Figure 3:
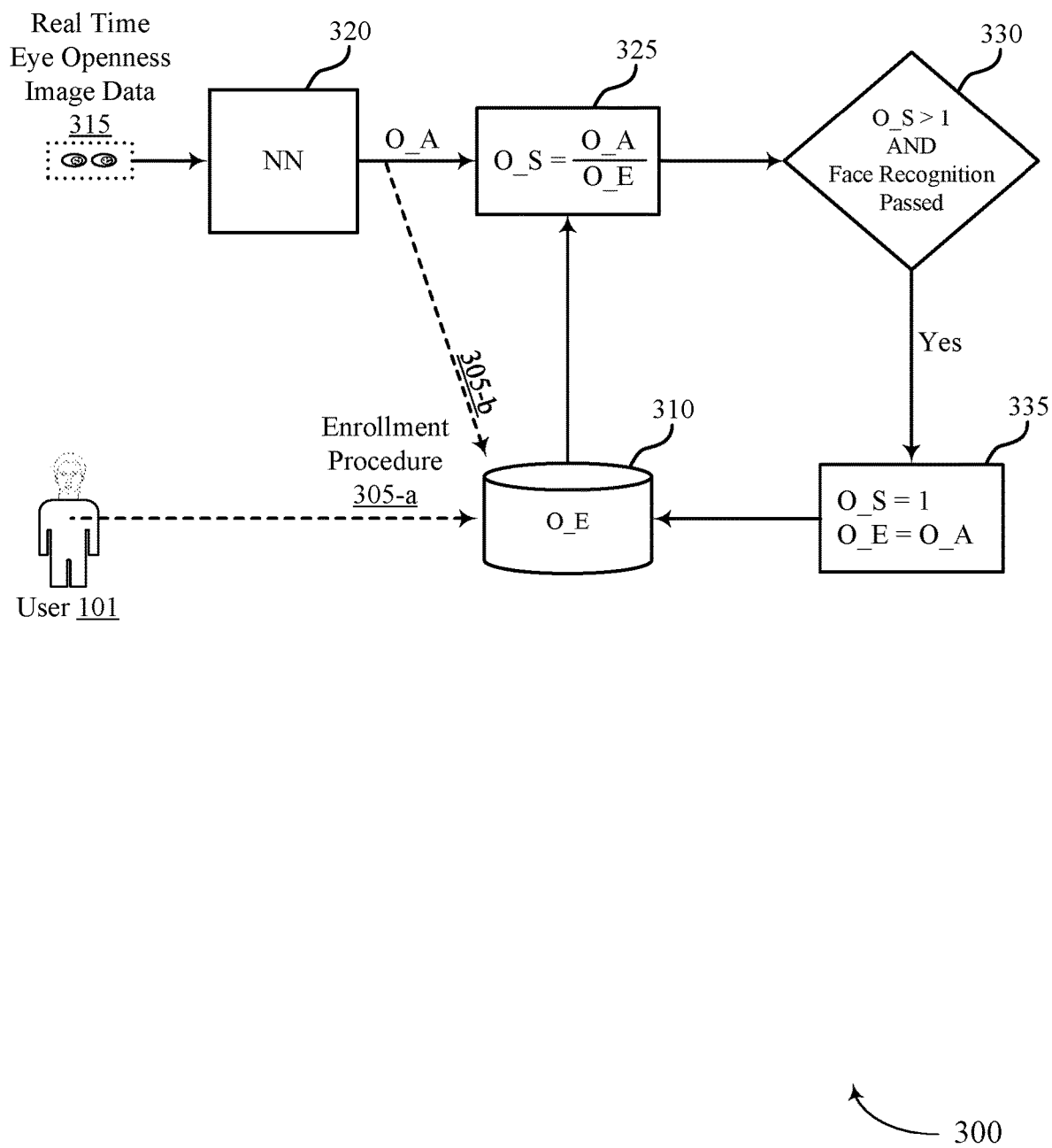
FIG. 3 illustrates an example of a flowchart that supports personalized eye openness estimation in accordance with aspects of the present disclosure.

FIG. 3 illustrates an example of a flowchart 300 that supports personalized eye openness estimation in accordance with aspects of the present disclosure. In some examples, flowchart 300 may implement aspects of system 100. For example, flowchart 300 may illustrate aspects of how a device may adapt or scale an eye openness estimation to consider user specific eye size (e.g., how a device may estimate personalized or user specific eye openness). Specifically, flowchart 300 illustrates user eye size enrollment, user specific eye openness estimation based on user maximum eye openness level, and, in some cases, updating of user maximum eye openness level information. In the following description of the flowchart 300, the operations of a device or user may be performed in a different order or at different times than the exemplary order shown. In some cases, certain operations may also be left out of the flowchart 300, or other operations may be added to the flowchart 300.

At 305, a device may perform an enrollment procedure (e.g., a user enrollment procedure, a user baseline eye openness enrollment procedure, a maximum eye openness enrollment procedure, etc.). In some cases, a user 101 may manually enter personalized maximum eye openness information at 305-a. For example, a device may interactively ask the user to input some thresholds on an eye openness level curve generated from the user. In other examples, a device may interactively ask the user to select an approximated eye size from a set of example eye sizes. Additionally or alternatively, the device may estimate a user specific eye size from faces enrolled on the device or from the first captured set of images or video frames at 305-b (e.g., an initial image may be used by the device to estimate a user specific eye size, or an initial image may be processed by the NN and the output may initially be set to equal the user specific maximum eye openness level).

At 310, a maximum eye openness level of a user 101 may be identified (e.g., identified or established based on the enrollment procedure at 305). As discussed herein, a maximum eye openness level (O_E) may be referred to as a user specific maximum eye openness level, a user baseline eye openness, a personalized eye size, etc.

At 315, a device (e.g., an image sensor) may capture real time eye openness image data (e.g., of user 101). Real time eye openness image data may refer to a single image, a video clip, a sequence of images, etc.

At 320, the real time eye openness image data may be passed through the trained neural network (NN). In some cases, the trained neural network may resemble aspects of network architecture 200, as described with reference to FIG. 2. As discussed above, the trained network (e.g., a trained neural network, a convolutional neural network, etc.) may output a scalar value (O_A) indicative of a degree of eye openness estimation. The degree of eye openness estimation may be estimated by the NN based on real time eye openness image data and a set of synthetic eye openness image data comprising known levels of eye openness (e.g., as the NN may be trained based on synthetic data and real data as described in more detail above). For example, in some cases, the NN may determine a level of eye openness based on a comparison of a feature vector generated from real time eye openness image data and feature vectors generated from the known synthetic data and annotated real data (e.g., based on a similarity between two vectors, such as a Euclidean distance or the like).

At 325, the device may estimate a user specific eye openness level (O_S) based on the estimated degree of eye openness (e.g., the scalar output of the NN) and the maximum eye openness level of the user. For example, in some cases, the user specific eye openness level may be determined as a ratio of the estimated degree of eye openness and the maximum eye openness level of the user $$\left(e.g., O\_S = \frac{O\_A}{O\_E}\right).$$

At 330, the device may determine whether to update the maximum eye openness level of the user. For example, if the device determines that the user specific eye openness level is greater than the maximum eye openness level, the device may decide to update the maximum eye openness level of the user. In some cases, the device may identify that $$O\_S = \frac{O\_A}{O\_E} > 1,$$

which may indicate the user specific eye openness level is greater than the maximum eye openness level. In some cases, the device may also determine whether a facial recognition condition has been satisfied before updating the maximum eye openness level of the user (e.g., to ensure another user with larger eyes does not update the maximum eye openness level of the original user). That is, in some cases, eye openness estimation techniques described herein may be tied together with facial recognition techniques (e.g., to load user enrollment information, to authorize maximum eye openness level updating for a particular user, etc.). In such cases, both $$O\_S > 1 \tag{1}$$

$$\text{MatchingScore}_{facialRecognitionM} > \text{Threshold}_{authentication} \tag{2}$$

conditions may be satisfied prior to updating of user maximum eye openness level.

At 335, the device may update the maximum eye openness level of the user in cases where the device decides to update the maximum eye openness level of the user at 330. For example, the device may update O_E to equal O_A (e.g., such that O_S=1). In such cases, the degree of eye openness estimated by the NN (O_A) may be set as the maximum eye openness level of the user (e.g., O_E=O_A).

As such, as a personalized multi-stage eye openness system continues to function, the user baseline eye openness (e.g., the personalized eye size) used to estimate user specific eye openness levels may be updated for improved accuracy of the system.

The operations of flowchart 300 may be implemented by a device or its components as described herein. For example, the operations of flowchart 300 may be performed by an eye openness manager as described with reference to FIGS. 4 and 5. In some examples, a device may execute a set of instructions to control the functional elements of the device to perform the functions described above. Additionally or alternatively, a device may perform aspects of the functions described above using special-purpose hardware.

Figure 4:
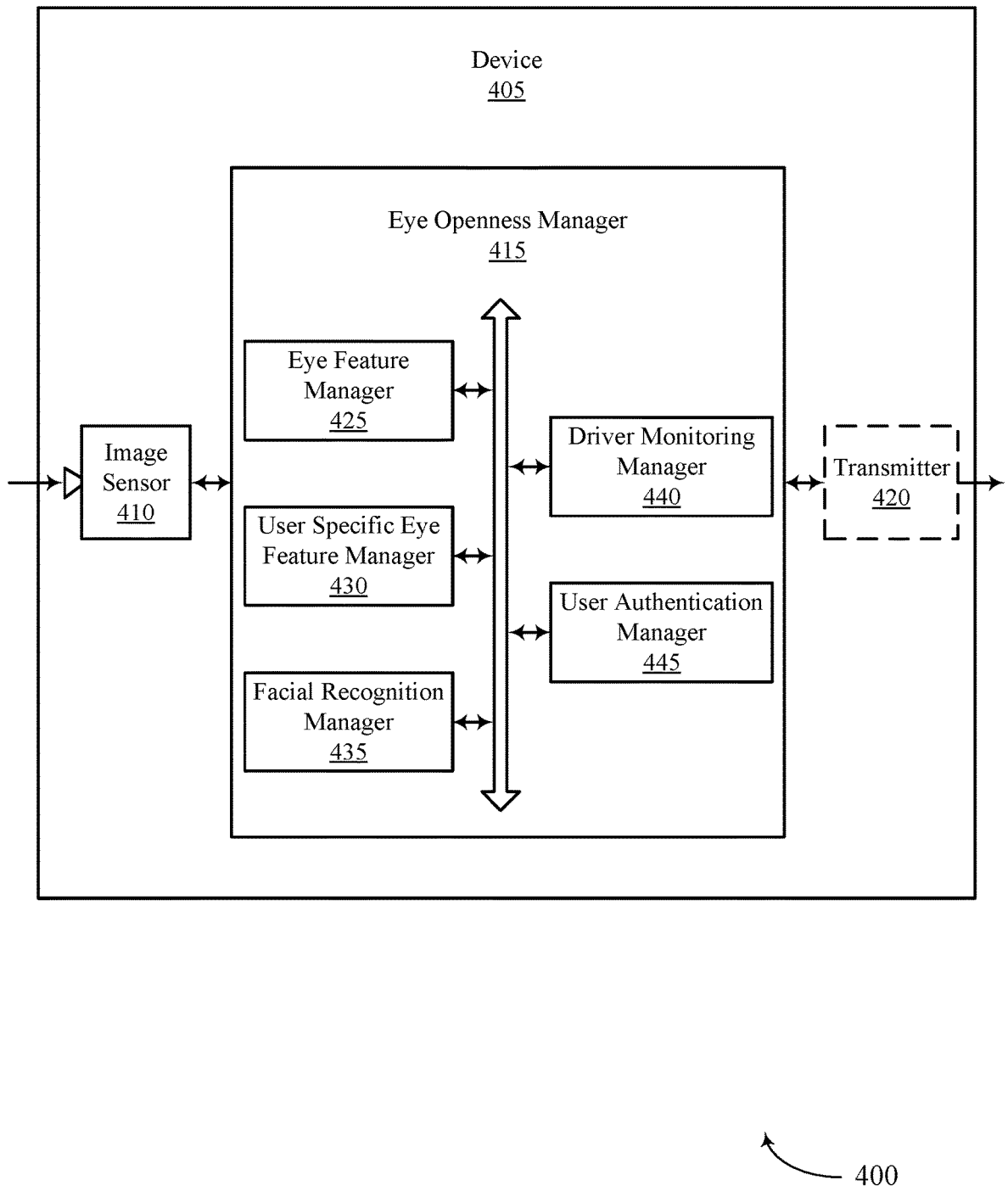
FIG. 4 shows a block diagram of a device that supports personalized eye openness estimation in accordance with aspects of the present disclosure.

FIG. 4 shows a block diagram 400 of a device 405 that supports personalized eye openness estimation in accordance with aspects of the present disclosure. The device 405 may be an example of aspects of a device 110 as described herein. The device 405 may include an image sensor 410 and an eye openness manager 415. The device 405 may also include a processor. In some example, the device 405 may include a transmitter 420. Each of these components may be in communication with one another (e.g., via one or more buses). In some cases, illustrated arrows may represent signals or information that may be communicated via electrical connections between device hardware.

The image sensor 410 (e.g., a camera) may receive information (e.g., light), which may be passed on to other components of the device 405. In some cases, the image sensor 410 may be an example of aspects of the I/O controller 515 described with reference to FIG. 5. As discussed above, the image sensor 410 may utilize one or more photosensitive elements that have a sensitivity to a spectrum of electromagnetic radiation to receive such information (e.g., to receive a pixel intensity value, RGB values of a pixel, etc.). For example, the image sensor 410 may capture real time eye openness image data. In some examples, the image sensor 410 may be an example of a means for capturing real time eye openness image data.

The eye openness manager 415 may capture real time eye openness image data (e.g., or receive real time eye openness image data from image sensor 410), estimate a degree of eye openness based on the real time eye openness image data and a set of synthetic eye openness image data including known levels of eye openness, identify a maximum eye openness level of a user during an enrollment procedure, where the maximum eye openness level is based on a personalized eye size of the user, estimate a user specific eye openness level based on the estimated degree of eye openness and the maximum eye openness level of the user, and trigger an action based on the estimated user specific eye openness level. The eye openness manager 415 may be an example of aspects of the eye openness manager 510 described herein. In some examples, the eye openness manager 415 may be an example of a means for estimating a degree of eye openness based at least in part on the real time eye openness image data and a set of synthetic eye openness image data comprising known levels of eye openness. In some examples, the eye openness manager 415 may be an example of a means for identifying a maximum eye openness level of a user during an enrollment procedure, wherein the maximum eye openness level is based on a personalized eye size of the user. In some examples, the eye openness manager 415 may be an example of a means for estimating a user specific eye openness level based at least in part on the estimated degree of eye openness and the maximum eye openness level of the user. In some examples, the eye openness manager 415 may be an example of a means for triggering an action based at least in part on the estimated user specific eye openness level.

The eye openness manager 415, or its sub-components, may be implemented in hardware, code (e.g., software or firmware) executed by a processor, or any combination thereof. If implemented in code executed by a processor, the functions of the eye openness manager 415, or its sub-components may be executed by a general-purpose processor, a DSP, an application-specific integrated circuit (ASIC), a FPGA or other programmable logic device, discrete gate or transistor logic, discrete hardware components, or any combination thereof designed to perform the functions described in the present disclosure.

The eye openness manager 415, or its sub-components, may be physically located at various positions, including being distributed such that portions of functions are implemented at different physical locations by one or more physical components. In some examples, the eye openness manager 415, or its sub-components, may be a separate and distinct component in accordance with various aspects of the present disclosure. In some examples, the eye openness manager 415, or its sub-components, may be combined with one or more other hardware components, including but not limited to an input/output (I/O) component, a transceiver, a network server, another computing device, one or more other components described in the present disclosure, or a combination thereof in accordance with various aspects of the present disclosure.

The eye openness manager 415 may be an example of aspects of an eye openness manager 510 described herein. The eye openness manager 415 may include an eye feature manager 425, a user specific eye feature manager 430, a driver monitoring manager 440, a facial recognition manager 435, and a user authentication manager 445. Each of these modules may communicate, directly or indirectly, with one another (e.g., via one or more buses). In some cases, the eye openness manager 415 may include the image sensor 410.

The image sensor 410 may capture real time eye openness image data. The eye feature manager 425 may estimate a degree of eye openness based on the real time eye openness image data and a set of synthetic eye openness image data including known levels of eye openness. In some examples, the eye feature manager 425 may estimate the degree of eye openness based on a MSE function, a binary loss function, and a distribution loss function. In some cases, the degree of eye openness is estimated based on convolution of the real time eye openness image data and the set of synthetic eye openness image data. In some cases, the real time eye openness image data includes a single image. In some cases, the real time eye openness image data may include a video clip or a sequence of images.

The user specific eye feature manager 430 may identify a maximum eye openness level of a user during an enrollment procedure, where the maximum eye openness level is based on a personalized eye size of the user (e.g., the user specific eye feature manager 430 may identify a user specific baseline eye size for personalized eye openness estimation). In some examples, the user specific eye feature manager 430 may receive a maximum eye openness level input from the user, where the maximum eye openness level is identified based on the maximum eye openness level input. In some cases, the maximum eye openness level is identified based on the real time eye openness image data. In some examples, the user specific eye feature manager 430 may determine that the user specific eye openness level is greater than the maximum eye openness level. In some examples, the user specific eye feature manager 430 may update the maximum eye openness level based on the determination. In some cases, the facial recognition manager 435 may determine the user has satisfied a facial recognition condition, and the maximum eye openness level may be updated based on the determination (e.g., based on the user satisfying a facial recognition condition).

The user specific eye feature manager 430 may estimate a user specific eye openness level based on the estimated degree of eye openness and the maximum eye openness level of the user. In some cases, the user specific eye openness level includes a percentage of eye openness (e.g., the user specific eye feature manager 430 may estimate a personalized degree of eye openness).

As discussed above, a device (e.g., device 405) may perform various actions based on multi-stage eye openness estimations. For example, in some cases, a driver monitoring manager 440 may trigger an action based on the estimated user specific eye openness level. In some examples, the driver monitoring manager 440 may trigger an alarm based on the estimated user specific eye openness level, where the estimated user specific eye openness level is below a threshold (e.g., a percentage of eye openness threshold indicating the driver may be fatigued, inebriated, falling asleep, etc.). In other examples, a user authentication manager 445 may trigger an action based on the estimated user specific eye openness level. The user authentication manager 445 may perform an authentication procedure based on the triggering, where the estimated user specific eye openness level exceeds a threshold (e.g., a percentage of eye openness threshold indicating the user is awake, is focusing on the device, is not distracted or looking away, etc.). In yet other examples, the facial recognition manager 435 may trigger an action based on the estimated user specific eye openness level. For example, the facial recognition manager 435 may trigger a facial recognition condition procedure based on the estimated user specific eye openness level exceeds a threshold (e.g., a percentage of eye openness threshold indicating the user is awake, is focusing on the device, is not distracted or looking away, etc.).

In some cases, the device 405 may include a transmitter 420. The transmitter 420 may transmit signals generated by other components of the device 405. In some examples, the transmitter 420 may be collocated with a receiver in a transceiver module. For example, the transmitter 420 may be an example of aspects of the transceiver 520 described with reference to FIG. 5. The transmitter 420 may utilize a single antenna or a set of antennas. In some examples, the transmitter 420 may transmit information (e.g., personalized multi-stage eye openness estimations) determined or estimated by the device 405 to another server (e.g., such as a driver monitoring system service center), to another device, etc.

Figure 5:
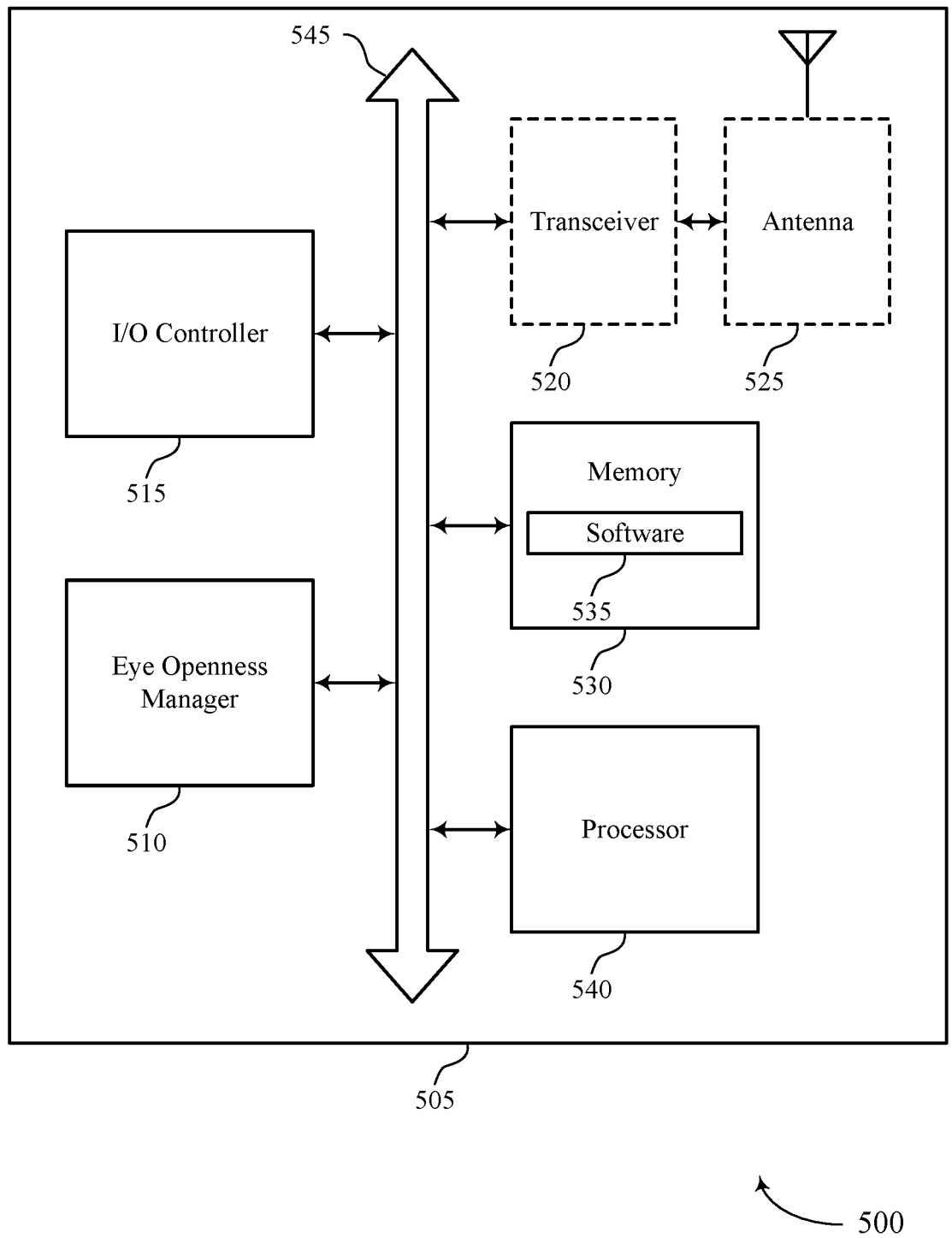
FIG. 5 shows a diagram of a system including a device that supports personalized eye openness estimation in accordance with aspects of the present disclosure.

FIG. 5 shows a diagram of a system 500 including a device 505 that supports personalized eye openness estimation in accordance with aspects of the present disclosure. The device 505 may be an example of or include the components of device 405 or a device 110 as described herein. In some example, the device 505 may include components for bi-directional voice and data communications including components for transmitting and receiving communications, including an eye openness manager 510, an I/O controller 515, memory 530, and a processor 540. In some cases, the device 505 may additionally include a transceiver 520 and an antenna 525 (e.g., to communicate aspects of personalized eye openness estimation information with other devices that may be implemented in a system, with a driver monitoring service center, etc.). These components may be in electronic communication via one or more buses (e.g., bus 545).

The eye openness manager 510 may capture real time eye openness image data (e.g., or receive real time eye openness image data from I/O controller 515), estimate a degree of eye openness based on the real time eye openness image data and a set of synthetic eye openness image data including known levels of eye openness, identify a maximum eye openness level of a user during an enrollment procedure, where the maximum eye openness level is based on a personalized eye size of the user, estimate a user specific eye openness level based on the estimated degree of eye openness and the maximum eye openness level of the user, and trigger an action based on the estimated user specific eye openness level.

The I/O controller 515 may manage input (e.g., pixel intensity values and/or RGB values of a pixel at an image sensor) and output signals (e.g., signals to trigger an action, etc.) for the device 505. In some example, the I/O controller 515 may include or refer to an image sensor, an alarm, etc., as described herein. The I/O controller 515 may also manage peripherals not integrated into the device 505. In some cases, the I/O controller 515 may represent a physical connection or port to an external peripheral. In some cases, the I/O controller 515 may utilize an operating system such as iOS®, ANDROID®, MS-DOS®, MS-WINDOWS®, OS/2®, UNIX®, LINUX®, or another known operating system. In other cases, the I/O controller 515 may represent or interact with a modem, a keyboard, a mouse, a touch-screen, or a similar device. In some cases, the I/O controller 515 may be implemented as part of a processor. In some cases, a user may interact with the device 505 via the I/O controller 515 or via hardware components controlled by the I/O controller 515.

The transceiver 520 may communicate bi-directionally, via one or more antennas, wired, or wireless links as described above. For example, the transceiver 520 may represent a wireless transceiver and may communicate bi-directionally with another wireless transceiver. The transceiver 520 may also include a modem to modulate the packets and provide the modulated packets to the antennas for transmission, and to demodulate packets received from the antennas. In some cases, the device may include a single antenna 525. However, in some cases the device may have more than one antenna 525, which may be capable of concurrently transmitting or receiving multiple wireless transmissions.

The memory 530 may include RAM and ROM. The memory 530 may store computer-readable, computer-executable code or software 535 including instructions that, when executed, cause the processor to perform various functions described herein. In some cases, the memory 530 may contain, among other things, a BIOS which may control basic hardware or software operation such as the interaction with peripheral components or devices.

The processor 540 may include an intelligent hardware device, (e.g., a general-purpose processor, a DSP, a CPU, a microcontroller, an ASIC, an FPGA, a programmable logic device, a discrete gate or transistor logic component, a discrete hardware component, or any combination thereof). In some cases, the processor 540 may be configured to operate a memory array using a memory controller. In other cases, a memory controller may be integrated into the processor 540. The processor 540 may be configured to execute computer-readable instructions stored in a memory (e.g., the memory 530) to cause the device 505 to perform various functions (e.g., functions or tasks supporting personalized eye openness estimation).

The software 535 may include instructions to implement aspects of the present disclosure, including instructions to support detecting a degree to which an eye is open. The software 535 may be stored in a non-transitory computer-readable medium such as system memory or other type of memory. In some cases, the software 535 may not be directly executable by the processor 540 but may cause a computer (e.g., when compiled and executed) to perform functions described herein.

Figure 6:
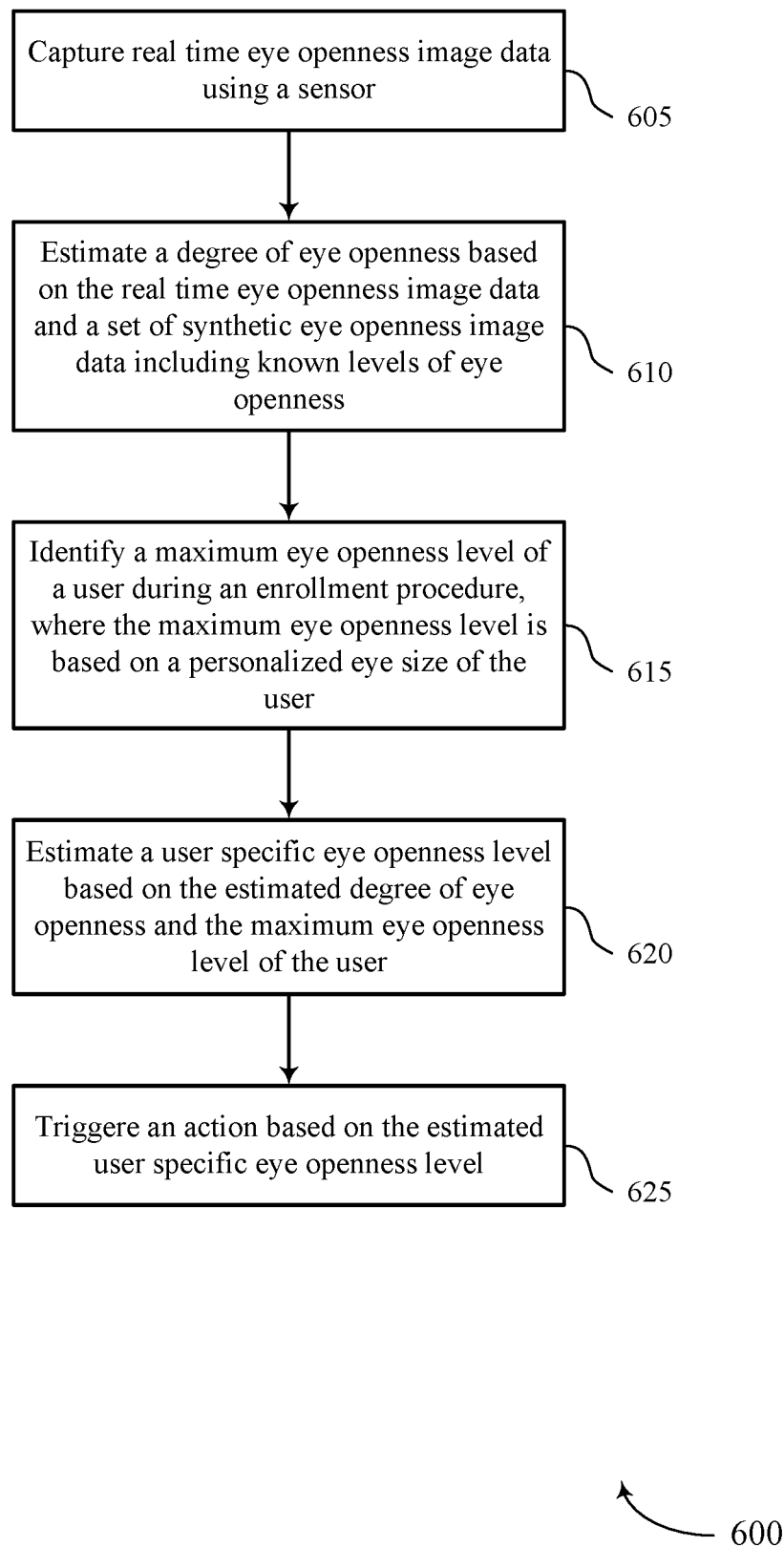
FIGS. 6 and 7 show flowcharts illustrating methods that support personalized eye openness estimation in accordance with aspects of the present disclosure.

FIG. 6 shows a flowchart illustrating a method 600 that supports personalized eye openness estimation in accordance with aspects of the present disclosure. The operations of method 600 may be implemented by a device or its components as described herein. For example, the operations of method 600 may be performed by an eye openness manager as described with reference to FIGS. 4 through 5. In some examples, a device may execute a set of instructions to control the functional elements of the device to perform the functions described below. Additionally or alternatively, a device may perform aspects of the functions described below using special-purpose hardware.

At 605, the device may capture real time eye openness image data (e.g., via an image sensor). The operations of 605 may be performed according to the methods described herein. In some examples, aspects of the operations of 605 may be performed by an image sensor as described with reference to FIGS. 4 through 5.

At 610, the device may estimate a degree of eye openness based on the real time eye openness image data and a set of synthetic eye openness image data including known levels of eye openness. The operations of 610 may be performed according to the methods described herein. In some examples, aspects of the operations of 610 may be performed by an eye feature manager as described with reference to FIGS. 4 through 5.

At 615, the device may identify a maximum eye openness level of a user during an enrollment procedure, where the maximum eye openness level is based on a personalized eye size of the user. The operations of 615 may be performed according to the methods described herein. In some examples, aspects of the operations of 615 may be performed by a user specific eye feature manager as described with reference to FIGS. 4 through 5.

At 620, the device may estimate a user specific eye openness level based on the estimated degree of eye openness and the maximum eye openness level of the user. The operations of 620 may be performed according to the methods described herein. In some examples, aspects of the operations of 620 may be performed by a user specific eye feature manager as described with reference to FIGS. 4 through 5.

At 625, the device may trigger an action based on the estimated user specific eye openness level. The operations of 625 may be performed according to the methods described herein. In some examples, aspects of the operations of 625 may be performed by a driver monitoring manager, a user authentication manager, etc., as described with reference to FIGS. 4 through 5.

Figure 7:
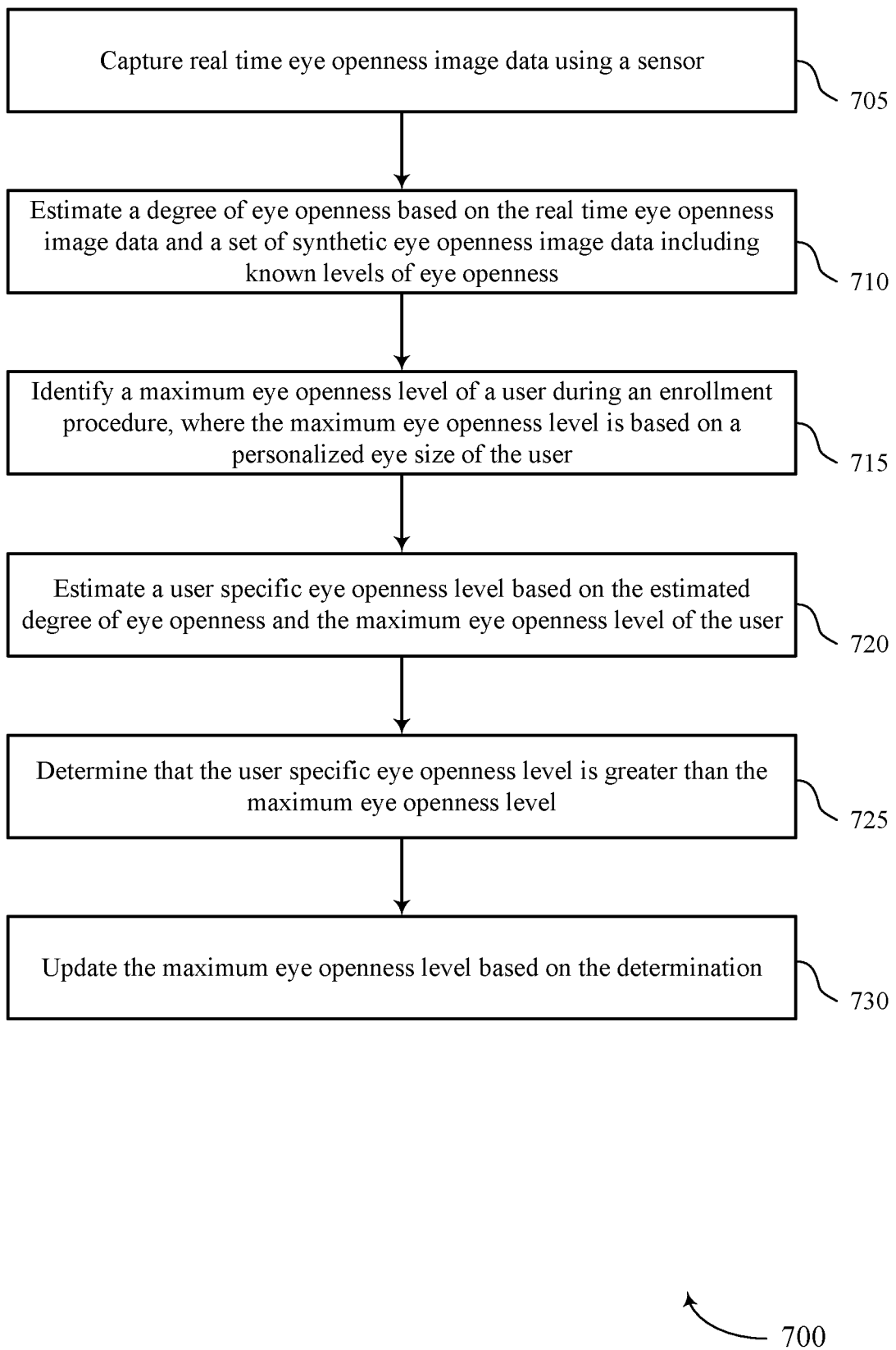

FIG. 7 shows a flowchart illustrating a method 700 that supports personalized eye openness estimation in accordance with aspects of the present disclosure. The operations of method 700 may be implemented by a device or its components as described herein. For example, the operations of method 700 may be performed by an eye openness manager as described with reference to FIGS. 4 through 5. In some examples, a device may execute a set of instructions to control the functional elements of the device to perform the functions described below. Additionally or alternatively, a device may perform aspects of the functions described below using special-purpose hardware.

At 705, the device may capture real time eye openness image data. The operations of 705 may be performed according to the methods described herein. In some examples, aspects of the operations of 705 may be performed by an image sensor as described with reference to FIGS. 4 through 5.

At 710, the device may estimate a degree of eye openness based on the real time eye openness image data and a set of synthetic eye openness image data including known levels of eye openness. The operations of 710 may be performed according to the methods described herein. In some examples, aspects of the operations of 710 may be performed by an eye feature manager as described with reference to FIGS. 4 through 5.

At 715, the device may identify a maximum eye openness level of a user during an enrollment procedure, where the maximum eye openness level is based on a personalized eye size of the user. The operations of 715 may be performed according to the methods described herein. In some examples, aspects of the operations of 715 may be performed by a user specific eye feature manager as described with reference to FIGS. 4 through 5.

At 720, the device may estimate a user specific eye openness level based on the estimated degree of eye openness and the maximum eye openness level of the user. The operations of 720 may be performed according to the methods described herein. In some examples, aspects of the operations of 720 may be performed by a user specific eye feature manager as described with reference to FIGS. 4 through 5.

At 725, the device may determine that the user specific eye openness level is greater than the maximum eye openness level. For example, the device may determine that the user specific eye openness level is greater than the maximum eye openness level based on the degree of eye openness estimated at 710 exceeding the maximum eye openness level identified at 715. In some examples, the device may determine that the user specific eye openness level is greater than the maximum eye openness level based on the user specific eye openness level exceeding 100% (e.g., based on O_S>1). The operations of 725 may be performed according to the methods described herein. In some examples, aspects of the operations of 725 may be performed by a user specific eye feature manager as described with reference to FIGS. 4 through 5.

At 730, the device may update the maximum eye openness level based on the determination. For example, in some cases, the maximum eye openness level may be updated or set to equal the user specific eye openness level estimated at 720. In other examples, the maximum eye openness level may be updated or set to equal the degree of eye openness estimated at 710 (e.g., O_E=O_A). The operations of 730 may be performed according to the methods described herein. In some examples, aspects of the operations of 730 may be performed by a user specific eye feature manager as described with reference to FIGS. 4 through 5.

It should be noted that the methods described herein describe possible implementations, and that the operations and the steps may be rearranged or otherwise modified and that other implementations are possible. Further, aspects from two or more of the methods may be combined.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described herein may be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable read-only memory (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, digital subscriber line (DSL), or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A method for detecting a degree to which an eye is open, comprising:
   capturing real time eye openness image data using a sensor;
   estimating a degree of eye openness based at least in part on the real time eye openness image data and a set of synthetic eye openness image data comprising known levels of eye openness;
   identifying a maximum eye openness level of a user during an enrollment procedure, wherein the maximum eye openness level is based on a personalized eye size of the user;
   estimating a user specific eye openness level based at least in part on the estimated degree of eye openness and the maximum eye openness level of the user; and
   triggering an action based at least in part on the estimated user specific eye openness level.

2. The method of claim 1, further comprising:
   determining that the user specific eye openness level is greater than the maximum eye openness level; and
   updating the maximum eye openness level based at least in part on the determination.

3. The method of claim 2, further comprising:
   determining the user has satisfied a facial recognition condition, wherein the maximum eye openness level is updated based at least in part on the determination.

4. The method of claim 1, wherein the degree of eye openness is estimated based at least in part on convolution of the real time eye openness image data and the set of synthetic eye openness image data.

5. The method of claim 1, further comprising:
   receiving a maximum eye openness level input from the user, wherein the maximum eye openness level is identified based at least in part on the maximum eye openness level input.

6. The method of claim 1, wherein the maximum eye openness level is identified based at least in part on the real time eye openness image data.

7. The method of claim 1, further comprising:
   performing an authentication procedure based at least in part on the triggering, wherein the estimated user specific eye openness level exceeds a threshold.

8. The method of claim 1, wherein triggering the action comprises:
   triggering an alarm based at least in part on the estimated user specific eye openness level, wherein the estimated user specific eye openness level is below a threshold.

9. The method of claim 1, wherein the user specific eye openness level comprises a percentage of eye openness.

10. The method of claim 1, wherein the real time eye openness image data comprises a single image.

11. The method of claim 1, further comprising:
    estimating the degree of eye openness based at least in part on a mean squared error (MSE) function, a binary loss function, and a distribution loss function.

12. An apparatus for detecting a degree to which an eye is open, comprising:
    a processor,
    memory in electronic communication with the processor; and
    instructions stored in the memory and executable by the processor to cause the apparatus to:
      capture real time eye openness image data using a sensor;
      estimate a degree of eye openness based at least in part on the real time eye openness image data and a set of synthetic eye openness image data comprising known levels of eye openness;
      identify a maximum eye openness level of a user during an enrollment procedure, wherein the maximum eye openness level is based on a personalized eye size of the user;
      estimate a user specific eye openness level based at least in part on the estimated degree of eye openness and the maximum eye openness level of the user; and
      trigger an action based at least in part on the estimated user specific eye openness level.

13. The apparatus of claim 12, wherein the instructions are further executable by the processor to cause the apparatus to:
    determine that the user specific eye openness level is greater than the maximum eye openness level; and
    update the maximum eye openness level based at least in part on the determination.

14. The apparatus of claim 13, wherein the instructions are further executable by the processor to cause the apparatus to:
    determine the user has satisfied a facial recognition condition, wherein the maximum eye openness level is updated based at least in part on the determination.

15. The apparatus of claim 12, wherein the degree of eye openness is estimated based at least in part on convolution of the real time eye openness image data and the set of synthetic eye openness image data.

16. The apparatus of claim 12, wherein the instructions are further executable by the processor to cause the apparatus to:
    receive a maximum eye openness level input from the user, wherein the maximum eye openness level is identified based at least in part on the maximum eye openness level input.

17. The apparatus of claim 12, wherein the maximum eye openness level is identified based at least in part on the real time eye openness image data.

18. The apparatus of claim 12, wherein the instructions are further executable by the processor to cause the apparatus to:
    perform an authentication procedure based at least in part on the triggering, wherein the estimated user specific eye openness level exceeds a threshold.

19. The apparatus of claim 12, wherein the instructions to trigger the action are executable by the processor to cause the apparatus to:
    trigger an alarm based at least in part on the estimated user specific eye openness level, wherein the estimated user specific eye openness level is below a threshold.

20. An apparatus for detecting a degree to which an eye is open, comprising:
- means for capturing real time eye openness image data using a sensor;
- means for estimating a degree of eye openness based at least in part on the real time eye openness image data and a set of synthetic eye openness image data comprising known levels of eye openness;
- means for identifying a maximum eye openness level of a user during an enrollment procedure, wherein the maximum eye openness level is based on a personalized eye size of the user;
- means for estimating a user specific eye openness level based at least in part on the estimated degree of eye openness and the maximum eye openness level of the user; and
- means for triggering an action based at least in part on the estimated user specific eye openness level.

\* \* \* \* \*